US011028045B2

(12) United States Patent
Ni

(10) Patent No.: US 11,028,045 B2
(45) Date of Patent: Jun. 8, 2021

(54) PROCESS FOR REDUCING CPI IN A DINITRILE STREAM

(71) Applicant: INV Nylon Chemicals Americas, LLC, Wilmington, DE (US)

(72) Inventor: Chengbao Ni, Beaumont, TX (US)

(73) Assignee: INV NYLON CHEMICALS AMERICAS, LLC, Wilmington, DE (US)

(*) Notice: Subject to any disclaimer, the term of this patent is extended or adjusted under 35 U.S.C. 154(b) by 0 days.

(21) Appl. No.: 16/095,793

(22) PCT Filed: Apr. 27, 2017

(86) PCT No.: PCT/US2017/029810
§ 371 (c)(1),
(2) Date: Oct. 23, 2018

(87) PCT Pub. No.: WO2017/192350
PCT Pub. Date: Nov. 9, 2017

(65) Prior Publication Data
US 2019/0135736 A1  May 9, 2019

Related U.S. Application Data

(60) Provisional application No. 62/330,380, filed on May 2, 2016.

(51) Int. Cl.
C07C 253/34 (2006.01)
B01D 3/00 (2006.01)
B01D 3/34 (2006.01)

(52) U.S. Cl.
CPC ............ *C07C 253/34* (2013.01); *B01D 3/009* (2013.01); *B01D 3/34* (2013.01)

(58) Field of Classification Search
CPC .......... C07C 253/34; B01D 3/009; B01D 3/34
See application file for complete search history.

(56) References Cited

U.S. PATENT DOCUMENTS

| | | | |
|---|---|---|---|
| 2,318,730 A | 5/1943 | Wilson | |
| 2,748,065 A * | 5/1956 | Trieschmann | C07C 255/00 203/38 |
| 2,768,132 A * | 10/1956 | Halliwell | C07C 253/34 203/33 |
| 2,841,537 A | 7/1958 | Guyer et al. | |
| 3,223,724 A | 12/1965 | Adam et al. | |
| 3,325,531 A * | 6/1967 | Mather | C07C 255/00 558/311 |
| 3,496,212 A | 2/1970 | Davison et al. | |
| 3,758,545 A | 9/1973 | Pounder et al. | |
| 3,775,258 A * | 11/1973 | Kershaw | C07C 255/00 203/29 |
| 3,819,491 A | 6/1974 | Moore et al. | |
| 3,839,408 A | 10/1974 | Arend et al. | |
| 4,235,767 A * | 11/1980 | Blount | C08G 73/0246 524/800 |
| 4,320,091 A | 3/1982 | Irvin | |
| 5,689,003 A | 11/1997 | Beatty et al. | |
| 5,900,511 A | 5/1999 | Sengupta et al. | |
| 6,084,121 A | 7/2000 | Rogers et al. | |
| 6,222,059 B1 | 4/2001 | Ebel et al. | |
| 6,331,651 B1 | 12/2001 | Ostermaier | |
| 7,453,012 B2 | 11/2008 | Bocquenet et al. | |
| 7,781,608 B2 | 8/2010 | Scheidel et al. | |
| 7,935,229 B2 | 5/2011 | Deckert et al. | |
| 2007/0155978 A1 | 7/2007 | Jungkamp et al. | |
| 2008/0076944 A1 | 3/2008 | Bartsch et al. | |
| 2008/0281119 A1 | 11/2008 | Scheidel et al. | |
| 2009/0270645 A1 | 10/2009 | Haderlein et al. | |
| 2010/0087684 A1 | 4/2010 | Do et al. | |
| 2011/0092749 A1 | 4/2011 | Sawant et al. | |

FOREIGN PATENT DOCUMENTS

| | | |
|---|---|---|
| CA | 672712 A | 10/1963 |
| CA | 796343 A | 10/1968 |
| CA | 912036 A | 10/1972 |
| CA | 1043813 A | 12/1978 |
| CN | 1681773 A | 10/2005 |
| CN | 1835915 A | 9/2006 |
| CN | 1914216 A | 2/2007 |
| CN | 101027252 A | 8/2007 |
| DE | 591269 C | 1/1934 |
| DE | 927089 C | 4/1955 |
| GB | 731458 A | 6/1955 |
| GB | 772979 A | 4/1957 |
| GB | 988622 A | 4/1965 |
| GB | 1094908 A | 12/1967 |
| JP | 2007-519670 A | 7/2007 |
| NL | 6407998 A | 1/1965 |
| WO | 2002/026698 A1 | 4/2002 |
| WO | 2004/080924 A2 | 9/2004 |
| WO | 2005/073174 A1 | 8/2005 |
| WO | 2007/141404 A1 | 12/2007 |
| WO | 2008/157218 A1 | 12/2008 |
| WO | 2008/157218 A4 | 2/2009 |
| WO | 2017/192350 A1 | 11/2017 |

OTHER PUBLICATIONS

Perry et al., "Liquid-Solid Operations and Equipment", Perry's Chemical Engineers' Handbook. 7th ed. New York: McGraw-Hill, 1997, pp. 18-34.
International Search Report and Written Opinion received for PCT Application No. PCT/US2017/029810, dated Jul. 17, 2017, 9 pages.
Derivatives of N-substituted imino-2-cyanocyclopentane, M. Maurice Lamant et al, Compt. Rend.1954, 238, 1591-1593.
Office Action received for Chinese patent application No. 201780024734.5, dated Oct. 20, 2020, 11 pages (3 pages English Translation and 8 pages original document).

* cited by examiner

*Primary Examiner* — Amanda L. Aguirre

(57) ABSTRACT

Disclosed is a process for removing 2-cyanocyclopentylideneimine (CPI) from a mixture containing CPI and dinitrile. The process comprises reacting CPI with an amine. The reaction may take place in the presence of water, and optionally, a catalyst. CPI is converted to products with a low volatility compared to the dinitrile.

21 Claims, No Drawings

PROCESS FOR REDUCING CPI IN A DINITRILE STREAM

FIELD

The present disclosure relates to the removal/reduction of 2-cyanocyclopentylideneimine (CPI) from dinitrile streams by reactions with organic amines. The reactions may take place in the presence of water, and optionally, a catalyst. In this process, CPI is converted into high boiling impurities that can be separated from dinitrile streams by distillation.

BACKGROUND

Dinitriles, including adiponitrile (ADN) and 2-methylglutaronitrile (MGN), are common nylon intermediates. These intermediates are usually produced by hydrocyanation reactions and contain impurities that have close boiling points to those of the dinitriles (ADN and/or MGN). CPI is an example of such an impurity that cannot be removed efficiently in industrial scale distillation columns. During the hydrogenation of dinitriles to their corresponding diamines (e.g. ADN to hexamethylenediamine (HMD), MGN to 2-methylpentamethylenediamine (MPMD)), CPI is hydrogenated to aminomethylcyclopenylamine (AMC), which is very difficult to separate from HMD or MPMD by distillation. The presence of AMC in diamines causes quality issues when the diamines are converted into polymers.

The removal of CPI from dinitriles, especially from ADN, has been addressed in the past. For example, U.S. Pat. No. 2,841,537 discloses the use of activated carbon to remove CPI from dinitrile streams. Canadian patent CA1043813A1 discloses the removal of CPI using weak-acid cation exchange resins. In both processes, the physical adsorption of CPI on the adsorbents might require frequent changes or regenerations of the adsorbents.

In addition, CPI can be hydrolyzed to 2-cyanocyclopentanone (CCPK), which is then separated from dinitrile streams. For example, U.S. Pat. No. 3,819,491 discloses the hydrolysis of CPI by heating crude ADN with water to a temperature of 140 to 280° C. without the addition of inorganic additives. In several other related patents, the acid catalyzed hydrolysis of CPI has been disclosed. For example, U.S. Pat. No. 3,775,258 and Canadian patent CA912,036 describe the hydrolysis of CPI between 140 to 210° C. with solid acid catalysts, including silica-alumina, crystalline aluminosilicates, boron phosphate, and titania-alumina. The use of acidic bisulfate salts of sodium, potassium, ammonium, magnesium, iron, manganese, zinc, cobalt, or nickel for the hydrolysis of CPI is disclosed in U.S. Pat. No. 3,223,724. In GB731,458, the hydrolysis of CPI by several acids, including $H_2SO_4$, $H_3PO_4$, HCl, adipic acid, and benzoic acid is disclosed. A common feature of these processes is the hydrolysis of CPI to form CCPK and the removal/separation of CCPK from dinitriles (mostly ADN) via distillation. It should be noted that the separation CCPK from dinitriles is usually not efficient in industrial distillation columns. For example, CCPK has a boiling point that is closer to MGN than CPI, rendering the removal of CCPK from MGN by distillation very difficult and inefficient.

Reaction-based processes for the removal/reduction of CPI from dinitriles have also been addressed in several patents. For example, CA672712 and WO2008/157218 disclose the treatment of CPI contaminated ADN with ozone, during which process, CPI is destroyed to form other byproducts that could be separated from ADN and/or HMD. U.S. Pat. No. 2,768,132 discloses the removal of CPI from ADN by contacting ADN with hydroxylamine salts of hydrochloric, nitric, sulfuric, and phosphoric acids at a temperature between 100 and 250° C. followed by distillation. The treatment of CPI contaminated ADN with an aldehyde, such as paraformaldehyde, to convert CPI into water-soluble derivatives or high-boilers is disclosed in U.S. Pat. Nos. 3,496,212 and 3,758,545. Given the feasibility of removing CPI by these processes, other impurities (e.g. additives and/or byproducts) that are introduced into the dinitrile streams require further purification steps.

As an imine, CPI reacts with organic amines to form N-substituted imine derivatives. For example, the direct reaction of CPI with aniline under reflux conditions (~150° C.) to form N-phenylimino-2-cyanocyclopentane was reported in Compt. Rend. 1954, 238, 1591-1593. When similar reactions were conducted with other amines, including HMD, 1,2-diamino-cyclohexane (DCH), or MPMD at low concentrations (~3% of CPI and ~3% of amine) in MGN, it was found that the reactions were very slow (e.g. <10% conversion in 2 hours at 190° C.), rendering such an approach (direct reaction of CPI with amines) impractical for the removal of CPI at an industrial scale.

SUMMARY

The present disclosure relates to a process for removing and/or reducing at least a portion of the amount of 2-cyanocyclopentylideneimine (CPI) from a mixture containing CPI and at least one dinitrile. The process comprises reacting CPI in the mixture with an amine. The reaction may take place in the presence of water, and optionally, a catalyst.

One aspect of the present disclosure is a process for removing CPI from a mixture containing at least one dinitrile comprising reacting the CPI with an amine in the presence of water.

In one aspect of the disclosed process, the reaction occurs at a temperature between ≥150 and ≤290° C.

In one aspect of the disclosed process, the molar ratio of amine groups to CPI is ≥1.0.

In a further aspect of the disclosed process, the mole ratio of water to CPI is ≥5.0.

In another aspect of the disclosed process, the molar ratio of CPI to dinitrile in the mixture is reduced by at least 25%.

One aspect of the disclosed process further comprises separating the low volatility reaction products from the dinitrile by distillation.

Another aspect of the present disclosure is a method for removing CPI from dinitrile, the method comprising; a) reacting the CPI with an amine in the presence of dinitrile, water and a catalyst to form a separable component; and b) separating at least a portion of the separable component from the dinitrile.

DESCRIPTION

The term "amine" is used in its usual sense, that is, an organic compound that can be derived from replacing one hydrogen in an ammonia molecule with a carbon-containing substituent R group. The amine contains at least one primary amine group ($-NH_2$). The R group in the amine can itself contain a substituted ammonia group, as in the case of a diamine. The R group can comprise any suitable carbon structure, including an alkyl group (linear or branched), a cycloalkyl group, or an aryl group, which can include unsaturated bonds.

By doing so it can for most applications within the present disclosure be surprisingly observed that the CPI is converted to a product or products with a low volatility compared to the at least one dinitrile. "Volatility" is used in its usual sense, that is, the tendency of a material to pass into the vapor state under a given combination of temperature and pressure. Perry, R. H. and Green, D. W. (Editors) (1997). Perry's Chemical Engineers' Handbook (7th ed.). McGraw-Hill. ISBN 0-07-049841-5.

These low volatile product(s) according to most application within the present disclosure can then easily be separated from the dinitrile-containing mixture by distillation, using conventional means.

Disclosed is a process for removing and/or reducing CPI from a mixture containing at least one dinitrile comprising reacting CPI with an amine in the presence of water, and optionally, a catalyst.

While not to limit the scope of the disclosure by a recitation of a theoretical mechanism, examples of chemical reactions of CPI with organic amines are illustrated below:

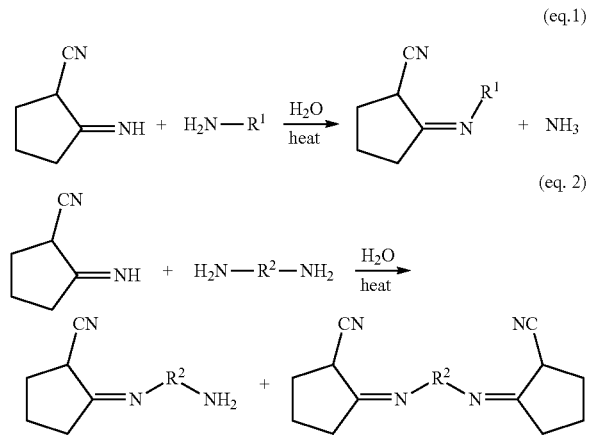

According to one embodiment of the present disclosure, the amine is an aliphatic mono- or diamine. In another embodiment of the present disclosure, the amine is an aromatic mono- or diamine.

According to another embodiment of the disclosure, the amine comprises a molecule of the structure $H_2N-R^1$. This structure represents a mono, primary amine.

For example, $R^1$ can be selected from the group consisting of $C_{1-18}$ alkyl, $C_{6-18}$ aryl, and $C_{3-18}$ cycloalkyl radicals. Examples of primary monoamines include but not limited to methylamine, ethylamine, cyclohexylamine, aniline, and substituted anilines, in which one or more substitutions takes place on the aromatic ring.

The amine may have the structure $H_2N-R^2-NH_2$. $R^2$ may be selected from the group consisting of $C_{2-18}$ alkenyl, $C_{6-18}$ areneyl, and $C_{3-18}$ cycloalkenyl radicals; for example $C_{2-18}$ radicals, for example $C_{4-10}$ radicals, for example $C_{5-8}$ radicals. Examples of amines of the structure $H_2N-R^2-NH_2$ include ethylenediamine, 1,3-diaminopropane, hexamethylenediamine, 2-methylpentamethylenediamine, 1,2-diamino-cyclohexane, o-phenylenediamine, m-phenylenediamine, p-phenylenediamine, N,N-dimethylethylenediamine, and diethylenetriamine. Certain amines with the structure $H_2N-R^2-NH_2$ are commercially available under trade-name Dytek® amines from INVISTA S.à r.l. These commercially available amines include hexamethylenediamine (HMD), 2-methylpentamethylenediamine (MPMD), aminomethylcyclopenylamine (AMC), 1,2-diaminocyclohexane (DCH), 1,3-diaminopentane.

The radicals $R_1$ and $R_2$ may contain substituents, heteroatoms or linkage groups. Examples of amines with a linkage group which contains a heteroatom include $NH_2-CH_2-CH_2-O-CH_2-CH_2-NH_2$, or $NH_2-CH_2-CH_2-NH-CH_2-CH_2-NH_2$.

The dinitrile can be a straight chain, branched or cyclic dinitrile or mixtures thereof. Examples of straight-chain dinitriles include adiponitrile, and examples of branched-chain dinitriles include methylglutaronitrile and 2-ethylsuccinonitrile, merely to name two examples. Straight chain and branched dinitriles having normal boiling points between about 200° C. and 350° C. are suitable, for example between 250° C. and 300° C.

The process can be carried out at a temperature between ≥150 and ≤290° C. This has been shown to be advantageous, because then the reaction of the CPI occurs usually with a sufficient kinetic speed while degradation of the dinitrile can be avoided or at least greatly reduced. For example, the process is carried out at ≥170° C. to ≤270° C.; ≥180° C. to ≤220° C.; and ≥185° C. to ≤195° C.

The molar ratio of amine groups to CPI is ≥1.0, for example ≥2, ≥5 or ≥10, and is preferably ≤100, ≤50, ≤20 and ≤10. Diamines (by definition) contain two amine groups and count as two amine groups for determining the ratio of amine groups to CPI.

The molar ratio of water to CPI is ≥5 or ≥10, and can be ≤100, ≤50, ≤20 and ≤10. The water can be present in the solution as processed, or can be added separately. The water can be liquid, vapor or a combination of the two, depending on the operating pressure.

By removing CPI from the mixture comprising CPI and dinitrile, the molar ratio of CPI to dinitrile may be reduced. For example, the molar ratio of CPI to dinitrile may be reduced by at least 25%, for example, at least 50%, for example, at least 75%, for example, at least 90%.

A method is disclosed for reducing and/or removing CPI from dinitrile, the method comprising; a) reacting the CPI with an amine in the presence of dinitrile, water and a catalyst to form a separable component; and b) separating at least a portion of the separable component from the dinitrile.

In some embodiments, the catalyst is an acid catalyst. In other embodiments, the acid catalyst is a solid. Suitable solid acid catalysts can be selected from the group consisting of one or more of silica-alumina, crystalline aluminosilicate, boron phosphate and titania-alumina.

In some embodiments, the acid catalyst is at least one acidic bisulfate salt of sodium, potassium, ammonium, magnesium, iron, manganese, zinc, cobalt, or nickel. In other embodiments, the acid catalyst is at least one inorganic acid. The inorganic acid may be at least one of $H_2SO_4$, $H_3PO_4$, and HCl. In some other embodiments, the acid catalyst is at least one of organic acid. The organic acid may be at least one of adipic acid, benzoic acid or a mixture of the adipic acid and benzoic acid.

In some embodiments, the catalyst may comprise liquid acids, for example, HCl, $H_2SO_4$, and $H_3PO_4$; solid acids, for example, the Amberlyst® resins, tungstic acid, acidic alumina, hydrogen mordenite, bentonite and others; ammonium and amine salts, for example, the $NH_4Cl$, $(NH_4)_2SO_4$, HMD.2HCl salt, and others; acidic bisulfate salts $M(HSO_4)_n$, $M=NH_4$, Li, Na, K, (n=1); Mg, Ca, Fe, Mn, Co, Zn, Ni (n=2); and metal sulfates, for example, $FeSO_4$, $Fe_2(SO_4)_3$, $NiSO_4$.

Ammonia and/or other gaseous products of the reaction of the CPI with the amine can be removed via a vent. It is desirable to allow the ammonia and other gaseous products to vent to the extent possible consistent with maintaining the desired reaction pressure.

The low volatility reaction product or products can optionally be separated from the dinitrile by conventional distillation, and the dinitrile can be adiponitrile, 2-methylglutaronitrile or both. The distillation can be carried out in batch or continuous mode, although continuous distillation is preferred for commercial operation. The number of theoretical stages required is a function of the process conditions for the distillation, including reflux ratio.

The process of the present disclosure may be carried out in a suitable multi-phase, contacting device or series of contacting devices that are known in the chemical industry. Examples of such contacting devices may include, but are not limited to, co-current or counter-current liquid-liquid contactors, reactive distillation, stirred tanks, tube reactors, hydraulic cyclones, lift reactors with downcomers, or combinations thereof. The process can be carried out in series as well as in parallel connections with properly sized, connecting flow lines, instrumentation and controls. The skilled person in the field of chemical and industrial engineering knows various ways of mixing and feeding the reagents by using the mixing equipment such as static mixers, in-line mixers, stirred vessels, preheating the streams to proper temperatures by using direct or indirect heating with hot water, steam, hot oil or other available energy input systems, heat exchange by interchange for temperature control by using a variety of heat exchange surface area across the hot and cold sides, and other operational details for such processes. Such process design, engineering and operation/control combinations should be clear to the person skilled in the field of engineering.

Definitions

ADN means "adiponitrile".
CPI means "2-cyanocyclopentylideneimine".
HMD means "hexamethylenediamine".
MGN means "2-methylglutaronitrile".
MPMD means "2-methylpentamethylenediamine".
ESN means "2-ethylsuccinonitrile".
AMC means "aminomethylcyclopenylamine".
DCH means "1,2-diaminocyclohexane".

The term "ppm" or "ppmw" means parts per million by weight unless otherwise stated.

The term "dinitrile" means an organic compound comprising two nitrile groups, for example ADN.

The term "diamine" means an organic compound comprising two amine ($-NH_2$) groups, for example HMD.

Psig is pounds per square inch gauge pressure.

Analytical Test Method

A Gas Chromatography (GC) analytical method is used to determine the concentration of CPI in dinitrile samples. CPI is integrated and reported as one group based on the response factor derived from the linear calibration of suberonitrile. Sample components are separated by gas liquid chromatography and detected using a flame ionization detector (FID). Sec-butylbenzene is used as an internal standard. An Agilent 7890 GC (or equivalent) equipped with an automatic liquid sampler (ALS), capillary split/splitless inlet, and flame ionization detector or equivalent is used. A capillary column used for the separation is Varian CP-Sil 8 CB, 25 m×0.53 mm ID×2 μm Film thickness, 5% phenyl/95% dimethylpolysiloxane [Part No. or P/N CP 7631 or equivalent].

Reagents used are:
phenol, 99.9% Purity, CAS 108-95-2, Sigma Aldrich, [P/N 109843].
2,4-Xylenol (2,4-Dimethylphenol): 99.2% Purity, CAS 105-67-9, Acros, [P/N 40845].
MGN (2-methylglutaronitrile): 99.6% Purity, CAS, Sigma-Aldrich, [P/N 40845].
CPI, (2-cyclopentylideneimine) re-crystallized: 100% Purity, CAS 2321-76-8, Invista.
biphenyl: 99.5% Purity, CAS 92-52-4, Aldrich, [P/N 01817TA].
suberonitrile (1,6-dicyanohexane): 98% Purity, CAS 629-40-3, Aldrich, [P/N D78008].
BHT (2,6-Di-tert-butyl-4-methylphenol): 99.9% Purity, CAS 128-37-0, Aldrich, [P/N D4, 740-4].
sec-butylbenzene: 99%+ Purity, CAS 135-98-8, Aldrich, [P/N B90408].
acetone:99.9% Purity, CAS 67-64-1, Omnisolv, [P/N AX0120-8].
acetonitrile: 99.9% Purity, CAS 75-05-8, Omnisolv, [P/N AX0145-1].
toluene: 99.9% Purity, CAS 108-88-3, Omnisolv, [P/N TX0737-1].
Molecular Sieve Activated, type 3A (8-12 Mesh): J. T. Baker, CAS 2708-05.

Operating Conditions used are:
Temperatures
Inlet temperature: 250° C.
Detector temperature: 330° C.
Oven temp initial: 90° C.
Oven max temperature: 305° C.

| Temp Program Segment | Initial Temp (° C.) | Final Temp (° C.) | Rate (° C./Minute) | Hold Time (min.) | Total Time (min.) |
|---|---|---|---|---|---|
| 1 | 90 | 150 | 3 | 0 | 20 |
| 2 | 150 | 200 | 2 | 0 | 25 |
| 3 | 200 | 300 | 20 | 40 | 45 |

The sample injection volume is about 2 μl. The split ratio used is about 20:1 at nominal 80 mL/min split vent flow. The column head pressure is about 3 psig.

EXAMPLES

Example 1 (Comparative): Reaction of CPI with MPMD: No $H_2O$ Added

The following reactants were loaded into a reactor equipped with a magnetic stir bar: 560 g of a methylglutaronitrile (MGN) solution (CPI concentration=4300 ppm; CPI:MPMD molar ratio=1:3.3). The MGN solution contained 150 ppm of water. The reaction mixture was heated to 190° C. under nitrogen for 24 hours. GC analysis showed that the CPI concentration changed from 4225 ppm to 2310 ppm.

Example 2: Reaction of CPI with MPMD: With $H_2O$ Addition

The following reactants were loaded into a reactor equipped with a magnetic stir bar: 2.4 g of deionized water and 530 g of a MGN solution (CPI concentration=5300 ppm; CPI:MPMD molar ratio=1:2.8). The water concentration of the MGN solution was 3160 ppm. The reaction mixture was heated to 190° C. under nitrogen for 24 hours. GC analysis showed that the CPI concentration changed from 4550 ppm to 730 ppm.

Comparison of Examples 1 and 2 shows that the presence of water significantly increases the conversion of CPI.

Example 3: Reaction of CPI with MPMD: With $H_2O$ Addition

The following reactants were loaded into a reactor equipped with a magnetic stir bar: 3.9 g of deionized water and 520 g of a MGN solution (CPI concentration=8800 ppm; CPI:MPMD molar ratio=1:3.1). The water concentration of the MGN solution was 7810 ppm. The reaction mixture was heated to 120° C. under nitrogen for 67 hours. GC analysis showed that the CPI concentration changed from 8800 ppm to 6877 ppm.

A comparison of examples 2 and 3 shows a much higher level of conversion of CPI at the higher temperature.

Example 4: Reaction of CPI with MPMD: With $H_2O$ Addition

The following reactants were loaded into a reactor equipped with a magnetic stir bar: 5.4 g of deionized water and 510 g of a MGN solution (CPI concentration=6900 ppm; CPI:MPMD molar ratio=1:3.8). The water concentration of the MGN solution was 8200 ppm. The reaction mixture was heated to 190° C. under nitrogen for 24 hours. GC analysis showed that the CPI concentration changed from 6900 ppm to 237 ppm.

Comparison of Examples 2 and 4 shows that the use of higher levels of $H_2O$ and MPMD increases the CPI conversion.

Example 5: Reaction of CPI with MPMD: With $H_2O$ Addition

The following reactants were loaded into a reactor equipped with a magnetic stir bar: 5.4 g of deionized water and 490 g of a MGN solution (CPI concentration=4350 ppm; CPI to MPMD molar ratio=1:3.4). The water concentration of the MGN solution was 4960 ppm. The reaction mixture was heated to 190° C. under a slow flow of nitrogen for 24 hours. GC analysis showed that the CPI concentration changed from 4350 to 173 ppm.

Comparison of Examples 2 and 5 shows that the use of higher levels of $H_2O$ increases the CPI conversion.

Example 6: Reaction of CPI with MPMD: With $H_2O$ Addition

The following reactants were loaded into a reactor equipped with a magnetic stir bar: 2.6 g of deionized water and 552 g of a MGN solution (CPI concentration=5200 ppm; CPI:MPMD molar ratio=1:2.9). The water concentration of the MGN solution was 4435 ppm. The reaction mixture was heated to 170° C. under nitrogen for 24 hours. GC analysis showed that the CPI concentration changed from 5200 ppm to 1800 ppm.

Comparison of Examples 2 and 6 shows that lower temperatures give decreased levels of CPI conversion.

Example 7: Separation of CPI Reaction Products

The reaction between CPI and amine (MPMD in the examples) generates an amine-CPI adduct which boils at a higher temperature than MGN. The reaction products from any of Examples 2 to 6, containing primarily MGN, amine-CPI adduct and residual CPI, are charged to a continuous multistage distillative system equipped with a kettle reboiler, and overhead condenser that indirectly exchanges heat against plant cooling water with an average inlet temperature of 20° C. Adequate refluxing capability and rectifying/stripping stages are available in the distillative operation. For example, about 12 to 15 theoretical stages are provided for distillative separation.

The feed enters the distillative system as a liquid above the kettle reboiler at the column base. The feed may be preheated for efficient separation. The feed is primarily MGN with about 1-2 wt % of amine-CPI adduct and about 300-350 ppm CPI. The distillative column pressures and temperatures are maintained such as to provide necessary gas-liquid hydraulics and inter-phase contacting across each theoretical stage. For example, the overhead condenser temperature is about 30° C., the column head temperature is maintained to about 194-195° C. and the column base temperature is maintained to about 205° C. The column is operated under a steady vacuum of 100-120 mmHg (top)/120-150 mmHg (base). A small reflux ratio of about 0.1-0.5 is maintained throughout the separation.

The overhead liquid product from the condenser is refined MGN with 300-400 ppm CPI and non-detectable amine-CPI adduct. The column reboiler purge stream is concentrated in about 25% amine-CPI adduct and balance primarily MGN. Thus, by reacting CPI with an amine compound as disclosed here followed by distillative separation to purge out the low volatility amine-CPI adduct, an order of magnitude reduction of CPI in the starting dinitrile may be achieved. The low-CPI dinitrile, i.e., refined MGN in this example, can be further transformed into useful intermediates, such as MPMD, methylglutaric acids or esters thereof.

Components lighter than MGN, such as water and high volatility impurities, may be stripped ahead of the distillative system using an adequately sized stripping column. Other optimizations such as pump-arounds, side-streams, etc. can be carried out depending on the feed quality and separation efficiency.

Example 8: Reaction of CPI with HMD: No $H_2O$ or Catalyst Added

The following reactants were loaded into a reactor equipped with a magnetic stir bar: 3.0 g of a MGN solution (CPI concentration=3.34 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.34% to 2.85%.

Example 9: Reaction of CPI with HMD: With a Catalytic Amount of $H_2O$ Added The following reactants were loaded into a reactor equipped with a magnetic stir bar: 17 mg of deionized water and 3.0 g of a MGN solution (CPI concentration=3.34 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.34% to 2.49%.

Example 10: Reaction of CPI with HMD: With a Catalytic Amount of HCl and H₂O Added The following reactants were loaded into a reactor equipped with a magnetic stir bar: 17 mg of HCl solution (10 wt %, in H₂O) and 3.0 g of a MGN solution (CPI concentration=3.73 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.73% to 0.10%.

Results of examples 8-10 are summarized in the table below.

| | CPI concentrations | | |
|---|---|---|---|
| | initial | 2 hour | reduction |
| Example 8 | 3.34% | 2.85% | 14.7% |
| Example 9 | 3.34% | 2.49% | 25.4% |
| Example 10 | 3.73% | 0.10% | 97.3% |

A comparison of examples 8, 9, and 10 shows that the addition of HCl (in water) results in a much higher reduction of CPI than without any additive (example 8) or with the addition of water (example 9).

Example 11: Reaction of CPI with Diaminocyclohexane (DCH): With No H₂O or Catalyst Added The following reactants were loaded into a reactor equipped with a magnetic stir bar: 3.0 g of a MGN solution (CPI concentration=3.05 wt %; CPI:DCH molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.05% to 2.71%.

Example 12: Reaction of CPI with DCH: With a Catalytic Amount of HCl and H₂O Added The following reactants were loaded into a reactor equipped with a magnetic stir bar: 17 mg of HCl solution (10 wt %, in H₂O) and 3.0 g of a MGN solution (CPI concentration=3.05 wt %; CPI:DCH molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.05% to 0.19%.

Example 13: Reaction of CPI with MPMD: With No H₂O or Catalyst Added

The following reactants were loaded into a reactor equipped with a magnetic stir bar: 3.0 g of a MGN solution (CPI concentration=2.61 wt %; CPI:MPMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 2.61% to 2.26%.

Example 14: Reaction of CPI with MPMD: With a Catalytic Amount of HCl and H₂O Added The following reactants were loaded into a reactor equipped with a magnetic stir bar: 17 mg of HCl solution (10 wt %, in H₂O) and 3.0 g of a MGN solution (CPI concentration=2.61 wt %; CPI:MPMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 2.61% to 0.08%.

Example 15: Reaction of CPI with "the C Column Make": With No H₂O or Catalyst Note: "the C column make" is a mixture of organic amines, primarily HMD and DCH The following reactants were loaded into a reactor equipped with a magnetic stir bar: 3.0 g of a MGN solution (CPI concentration=3.20 wt %; CPI:amine molar ratio=~1). The reaction mixture was heated to 190° C. inside of a nitrogen purge box for 2 hours while the reactor was opened to the nitrogen atmosphere via a syringe needle. GC analysis showed that the CPI concentration changed from 3.20% to 2.57%.

Example 16: Reaction of CPI with "the C Column Make": With a Catalytic Amount of HCl and H₂O Added The following reactants were loaded into a reactor equipped with a magnetic stir bar: 17 mg of HCl solution (10 wt %, in H₂O) and 3.0 g of a MGN solution (CPI concentration=3.20 wt %; CPI:amine molar ratio=~1). The reaction mixture was heated to 190° C. inside of a nitrogen purge box for 2 hours while the reactor was opened to the nitrogen atmosphere via a syringe needle. GC analysis showed that the CPI concentration changed from 3.20% to 0.37%.

Results of examples 11-16 are summarized in the table below.

| | CPI concentrations | | |
|---|---|---|---|
| | initial | 2 hour | reduction |
| Example 11 | 3.05% | 2.71% | 11.1% |
| Example 12 | 3.05% | 0.19% | 93.8% |
| Example 13 | 2.61% | 2.26% | 11.1% |
| Example 14 | 2.61% | 0.08% | 96.9% |
| Example 15 | 3.20% | 2.57% | 19.7% |
| Example 16 | 3.20% | 0.37% | 88.4% |

A comparison of examples 11-16 shows that the addition of HCl (in water) into the CPI/amine mixture results in a much higher reduction of CPI than without the addition of HCl.

Example 17: Reaction of CPI with HMD: A Catalytic Amount of H₂SO₄ and H₂O Added The following reactants were loaded into a reactor equipped with a magnetic stir bar: 17 mg of H₂SO₄ solution (5 wt %, in H₂O) and 3.0 g of a MGN solution (CPI concentration=3.73 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.73% to 0.39%.

Example 18: Reaction of CPI with HMD: A
Catalytic Amount of $H_3PO_4$ and $H_2O$ Added The following reactants were loaded into a reactor equipped with a magnetic stir bar: 17 mg of $H_3PO_4$ solution (10 wt %, in $H_2O$) and 3.0 g of a MGN solution (CPI concentration=3.73 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.73% to 1.96%.

Results of examples 8-10, 17, and 18 are summarized in the table below.

| | CPI concentrations | | |
|---|---|---|---|
| | initial | 2 hour | reduction |
| Example 8 | 3.34% | 2.85% | 14.7% |
| Example 9 | 3.34% | 2.49% | 25.4% |
| Example 10 | 3.73% | 0.10% | 97.3% |
| Example 17 | 3.73% | 0.39% | 89.5% |
| Example 18 | 3.73% | 1.96% | 47.5% |

A comparison of examples 8-10, 17, and 18 shows that the addition of acids (HCl, $H_2SO_4$, or $H_3PO_4$) results in a higher reduction of CPI than without any additive (example 8) or with the addition of water alone (example 9).

Example 19: Reaction of CPI with HMD: A
Catalytic Amount of Dry Amberlyst® 36 Resin
Added The following reactants were loaded into a reactor equipped with a magnetic stir bar: 74 mg of dry Amberlyst® 36 resin and 3.0 g of a MGN solution (CPI concentration=2.99 wt %; CPI:HMD molar ratio=1:1.1). The dry Amberlyst® 36 resin is believed to contain at least some (e.g., ≤1.65%) water. The reaction mixture was heated to 190° C. inside of a nitrogen purge box for 2 hours while the reactor was opened to the nitrogen atmosphere via a syringe needle. GC analysis showed that the CPI concentration changed from 2.99% to 0.60%.

Example 20: Reaction of CPI with HMD: $H_2O$ and
Dry Amberlyst® 36 Resin Added

The following reactants were loaded into a reactor equipped with a magnetic stir bar: 74 mg of dry Amberlyst® 36 resin, 17 mg of deionized water, and 3.0 g of a MGN solution (CPI concentration=2.99 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 2.99% to 0.29%.

After GC analysis, the liquid in the reactor was decanted. 3.0 g of a MGN solution (CPI:HMD molar ratio=1:1.1) was added to the same reactor. The reaction mixture was conducted similarly to the 1st run. GC analysis showed that the CPI concentration changed from 2.77% to 0.68%. A 3rd run with the catalyst recycled for the 2nd time was conducted similarly to the 2nd run. GC analysis showed that the CPI concentration changed from 3.11% to 0.59%.

The CPI concentrations of the first, second and third runs are summarized in the following table.

| | CPI concentrations | | |
|---|---|---|---|
| | initial | 2 hour | reduction |
| 1st run | 2.99% | 0.29% | 90.3% |
| 2nd run | 2.77% | 0.68% | 75.5% |
| 3rd run | 3.31% | 0.59% | 82.2% |

The results from example 20 shows that the Amberlyst® 36 resin catalyst can be recycled for the reaction of CPI with amines.

Example 21: Reaction of CPI with HMD: A
Catalytic Amount of Tungstic Acid and $H_2O$ Added The following reactants were loaded into a reactor equipped with a magnetic stir bar: 50 mg of tungstic acid, 17 mg of deionized water, and 3.0 g of a MGN solution (CPI concentration=3.34 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.34% to 0.08%.

Example 22: Reaction of CPI with HMD: A
Catalytic Amount of Theta Alumina and $H_2O$
Added The following reactants were loaded into a reactor equipped with a magnetic stir bar: 100 mg of theta alumina, 17 mg of deionized water, and 3.0 g of a MGN solution (CPI concentration=3.34 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.34% to 0.75%.

Example 23: Reaction of CPI with HMD: A
Catalytic Amount of Acidic Silica Gel and $H_2O$ The following reactants were loaded into a reactor equipped with a magnetic stir bar: 100 mg of acidic silica gel, 17 mg of deionized water, and 3.0 g of a MGN solution (CPI concentration=3.34 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.34% to 1.92%.

Example 24: Reaction of CPI with HMD: A
Catalytic Amount of Hydrogen Mordenite and $H_2O$ The following reactants were loaded into a reactor equipped with a magnetic stir bar: 100 mg of hydrogen mordenite, 17 mg of deionized water, and 3.0 g of a MGN solution (CPI concentration=3.34 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.34% to 1.54%.

Example 25: Reaction of CPI with HMD: A
Catalytic Amount of Bentonite and $H_2O$ The following reactants were loaded into a reactor equipped with a magnetic stir bar: 100 mg of bentonite, 17 mg of deionized water, and 3.0 g of a MGN solution (CPI concentration=3.34 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.34% to 0.38%.

Results of examples 8, 9, 19, and 22-25 are summarized in the table below.

| | CPI concentrations | | |
|---|---|---|---|
| | initial | 2 hour | reduction |
| Example 8 | 3.34% | 2.85% | 14.7% |
| Example 9 | 3.34% | 2.49% | 25.4% |
| Example 19 | 2.99% | 0.60% | 79.9% |
| Example 21 | 3.34% | 0.08% | 97.6% |
| Example 22 | 3.34% | 0.75% | 77.5% |
| Example 23 | 3.34% | 1.92% | 42.5% |
| Example 24 | 3.34% | 1.54% | 53.9% |
| Example 25 | 3.34% | 0.38% | 88.6% |

A comparison of examples 8, 9, 19, and 21-25 shows that the addition of solid acids results in a higher reduction of CPI than without any additive (example 8) or with the addition of water (example 9).

Example 26: Reaction of CPI with HMD: A Catalytic Amount of HMD.2HCl Salt and $H_2O$ The following reactants were loaded into a reactor equipped with a magnetic stir bar: 30 mg of HMD.2HCl salt, 17 mg of deionized water, and 3.0 g of a MGN solution (CPI concentration=3.80 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.80% to 0.13%.

Example 27: Reaction of CPI with HMD: A Catalytic Amount of $H_2O$ and 2-Iminopiperidine.HCl The following reactants were loaded into a reactor equipped with a magnetic stir bar: 32 mg of 2-iminopiperidine.HCl salt, 17 mg of deionized water, and 3.0 g of a MGN solution (CPI concentration=3.80 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.80% to 0.13%.

Example 28: Reaction of CPI with HMD: A Catalytic Amount of $H_2O$ and $NH_4Cl$

The following reactants were loaded into a reactor equipped with a magnetic stir bar: 30 mg of $NH_4Cl$, 17 mg of deionized water, and 3.0 g of a MGN solution (CPI concentration=3.41 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.41% to 0.65%.

Example 29: Reaction of CPI with HMD: A Catalytic Amount of $H_2O$ and $(NH_4)_2SO_4$ The following reactants were loaded into a reactor equipped with a magnetic stir bar: 30 mg of $(NH_4)_2SO_4$, 17 mg of deionized water, and 3.0 g of a MGN solution (CPI concentration=3.34 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.34% to 0.13%.

Results of examples 8, 9, and 26-29 are summarized in the table below.

| | CPI concentrations | | |
|---|---|---|---|
| | initial | 2 hour | reduction |
| Example 8 | 3.34% | 2.85% | 14.7% |
| Example 9 | 3.34% | 2.49% | 25.4% |
| Example 26 | 3.80% | 0.13% | 96.6% |
| Example 27 | 3.80% | 0.13% | 96.6% |
| Example 28 | 3.41% | 0.65% | 80.9% |
| Example 29 | 3.34% | 0.13% | 96.1% |

A comparison of examples 8, 9, and 26-29 shows that the addition of ammonium salts of amines or $NH_3$ and water results in a higher reduction of CPI than without any additive (example 8) or with the addition of water (example 9).

Example 30: Reaction of CPI with HMD: A Catalytic Amount of $H_2O$ and $Fe_2(SO_4)_3$ The following reactants were loaded into a reactor equipped with a magnetic stir bar: 30 mg of $Fe_2(SO_4)_3$, 17 mg of deionized water, and 3.0 g of a MGN solution (CPI concentration=3.34 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.34% to 0.13%.

Example 31: Reaction of CPI with a Catalytic Amount of $H_2O$ and $NiSO_4.2H_2O$ The following reactants were loaded into a reactor equipped with a magnetic stir bar: 30 mg of $NiSO_4 2H_2O$, 17 mg of deionized water, and 3.0 g of a MGN solution (CPI concentration=3.34 wt %; CPI:HMD molar ratio=1:1.1). The reaction mixture was heated to 190° C. inside of a nitrogen purge box for 2 hours while the reactor was opened to the nitrogen atmosphere via a syringe needle. GC analysis showed that the CPI concentration changed from 3.34% to 0.93%.

Results of examples 8, 9, 30, and 31 are summarized in the table below.

| | CPI concentrations | | |
|---|---|---|---|
| | initial | 2 hour | reduction |
| Example 8 | 3.34% | 2.85% | 14.7% |
| Example 9 | 3.34% | 2.49% | 25.4% |
| Example 30 | 3.34% | 0.13% | 96.1% |
| Example 31 | 3.34% | 0.93% | 72.2% |

A comparison of examples 8, 9, and 30-31 shows that the addition of the transition metal salts of chloride and sulfate results in a higher reduction of CPI than without any additive (example 8) or with the addition of water (example 9).

While the illustrative embodiments of the disclosure have been described with particularity, it will be understood that various other modifications will be apparent to and may be readily made by those skilled in the art without departing from the spirit and scope of the disclosure. Accordingly, it is not intended that the scope of the claims hereof be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The invention claimed is:

1. A process for removing at least a portion of CPI from a mixture comprising CPI and at least one dinitrile, said process comprising reacting CPI in the mixture with an amine, wherein the amine is an aliphatic or aromatic amine.

2. The process of claim 1 wherein the dinitrile is selected from adiponitrile, methylglutaronitrile, ethylsuccinonitrile, and mixtures thereof.

3. The process of claim 1 wherein the reaction occurs at a temperature between $\geq 150$ and $\leq 290°$ C.

4. The process of claim 1 wherein a molar ratio of amine groups to CPI is $\geq 1.0$.

5. The process of claim 1, further comprising separating low volatility reaction products from the dinitrile by distillation.

6. The process of claim 1 wherein the dinitrile is adiponitrile, 2-methylglutaronitrile, or both.

7. The process of claim 1 wherein the aliphatic amine is a diamine.

8. The process of claim 1 wherein the diamine is hexamethylenediamine.

9. The process of claim 1 wherein CPI is reacted with the amine in the presence of water.

10. The process of claim 9 wherein a mole ratio of water to CPI is $\geq 5.0$.

11. A method for removing CPI from dinitrile, the method comprising:
reacting the CPI with an amine in the presence of a dinitrile, water and a catalyst to form a separable component; and
separating at least a portion of the separable component from the dinitrile.

12. The method of claim 11 wherein the dinitrile is adiponitrile, methylglutaronitrile, ethylsuccinonitrile, or mixtures thereof.

13. The method of claim 11 wherein the catalyst is an acid catalyst.

14. The method of claim 13 wherein the acid catalyst is a solid.

15. The method of claim 14 wherein the solid is chosen from silica-alumina, crystalline aluminosilicate, boron phosphate, titania-alumina, and mixtures thereof.

16. The method of claim 13 wherein the acid catalyst is at least one acidic bisulfate salt of sodium, potassium, ammonium, magnesium, iron, manganese, zinc, cobalt, or nickel.

17. The method of claim 13 wherein the acid catalyst is at least one inorganic acid.

18. The method of claim 17 wherein the inorganic acid is at least one of $H_2SO_4$, $H_3PO_4$, and HCl.

19. The method of claim 13 wherein the acid catalyst is adipic acid, benzoic acid, or a mixture of adipic acid and benzoic acid.

20. The method of claim 11 wherein the separating further comprises distilling.

21. The method of claim 20 wherein the distilling recovers the dinitrile from the separable component as a more volatile component than the separable component.

* * * * *